(12) United States Patent
Pachpande et al.

(10) Patent No.: US 11,807,591 B1
(45) Date of Patent: Nov. 7, 2023

(54) PROCESSES AND APPARATUSES FOR CONVERTING CARBON DIOXIDE INTO OLEFINS

(71) Applicant: UOP LLC, Des Plaines, IL (US)

(72) Inventors: Anil Nivrutti Pachpande, Gurugram (IN); Jan De Ren, Arlington Heights, IL (US); Yogesh Kumar Gupta, Gurugram (IN)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/817,418

(22) Filed: Aug. 4, 2022

(51) Int. Cl.
| | | |
|---|---|---|
| *C07C 1/20* | (2006.01) | |
| *C07C 27/06* | (2006.01) | |
| *C25B 1/04* | (2021.01) | |
| *C01B 32/40* | (2017.01) | |

(52) U.S. Cl.
CPC ............... *C07C 1/20* (2013.01); *C01B 32/40* (2017.08); *C07C 27/06* (2013.01); *C25B 1/04* (2013.01)

(58) Field of Classification Search
CPC ........... C07C 1/20; C07C 27/06; C01B 32/40; C25B 1/04
See application file for complete search history.

(56) References Cited

U.S. PATENT DOCUMENTS

| | | | | |
|---|---|---|---|---|
| 4,663,931 A | * | 5/1987 | Schiffers | C07C 51/12 60/39.12 |
| 4,676,063 A | * | 6/1987 | Goebel | F01K 23/068 60/39.12 |
| 5,312,843 A | * | 5/1994 | Yamauchi | C07C 29/1518 518/703 |
| 8,138,380 B2 | | 3/2012 | Olah et al. | |
| 8,212,088 B2 | | 7/2012 | Olah et al. | |
| 8,822,553 B1 | * | 9/2014 | Wenzel | C01B 3/02 48/210 |
| 8,911,520 B2 | | 12/2014 | Möller | |
| 8,937,103 B2 | | 1/2015 | Young | |
| 2002/0025457 A1 | * | 2/2002 | Dodd | C01B 3/0015 204/278 |
| 2006/0211777 A1 | * | 9/2006 | Severinsky | C01B 3/16 518/702 |
| 2007/0244208 A1 | * | 10/2007 | Shulenberger | C10K 3/026 518/726 |
| 2008/0040975 A1 | * | 2/2008 | Calderon | C10J 3/64 48/197 R |
| 2009/0289227 A1 | * | 11/2009 | Rising | C25B 1/00 422/600 |

(Continued)

FOREIGN PATENT DOCUMENTS

| | | |
|---|---|---|
| DE | 102015008145 A1 | 1/2017 |
| WO | 2016206669 A1 | 12/2016 |

OTHER PUBLICATIONS

Lahijani, Pooya et al., Conversion of the greenhouse gas CO2 to the fuel gas CO via Boudouard reaction: A review, Renewable and Sustainable Energy Reviews, vol. 41, Jan. 2015, pp. 615-632.

*Primary Examiner* — Ali Z Fadhel

(57) ABSTRACT

Processes and apparatuses for converting carbon dioxide into hydrocarbons. Carbon dioxide and coke are reacted in a reaction zone to produce carbon monoxide. The Carbon monoxide and a hydrogen stream are reacted to produce methanol. The methanol is reacted in reaction zone to produce ethylene and propylene. The hydrogen and the oxygen can be produced in an electrolysis zone that separates water into hydrogen and oxygen.

16 Claims, 2 Drawing Sheets

(56) References Cited

U.S. PATENT DOCUMENTS

Figure 1:
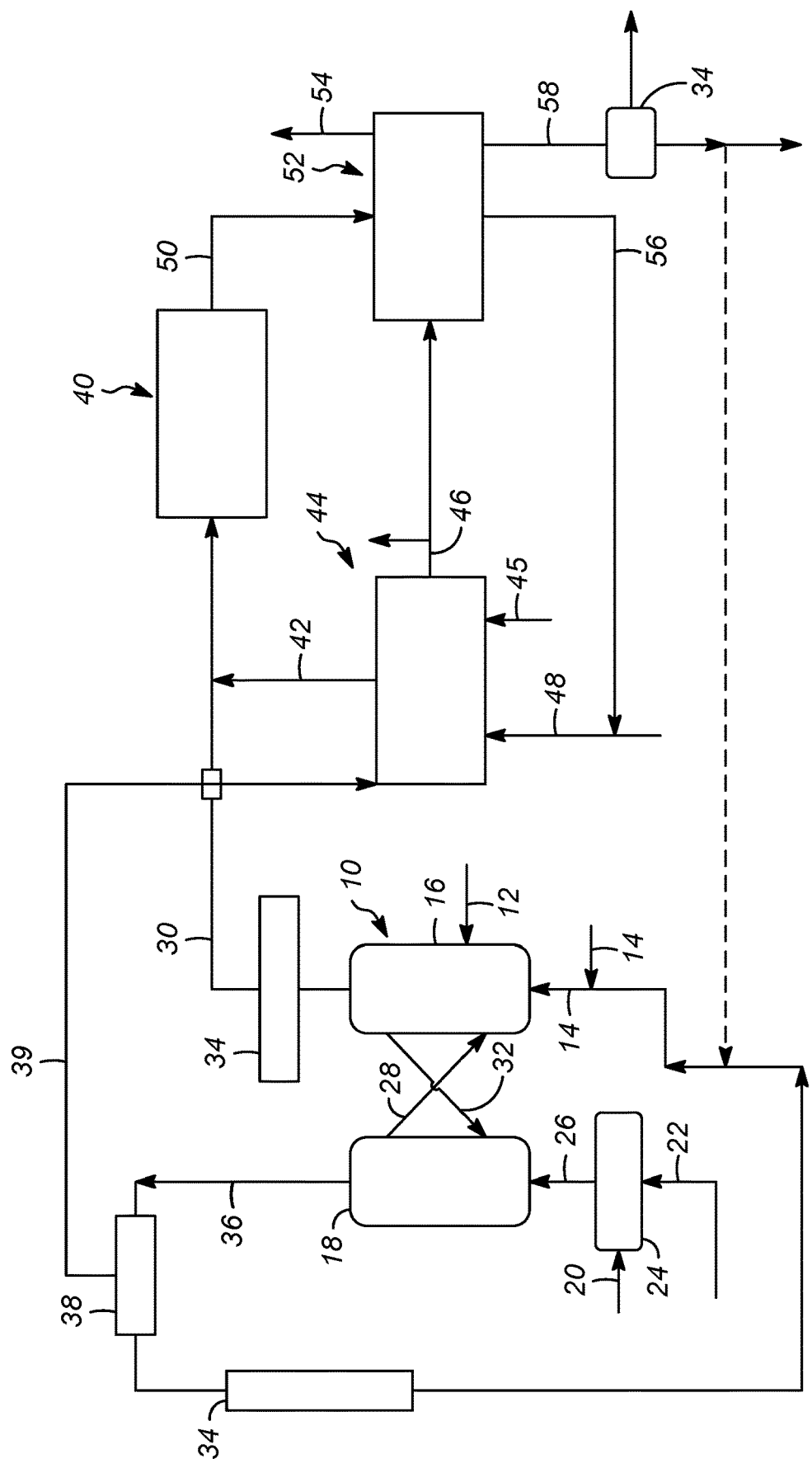

| | | | | |
|---|---|---|---|---|
| 2010/0137457 A1* | 6/2010 | Kaplan | ............... | C07C 29/1516 |
| | | | | 518/702 |
| 2014/0000157 A1* | 1/2014 | O'Connor | ................ | C10L 1/02 |
| | | | | 44/388 |
| 2019/0359894 A1* | 11/2019 | Heidel | ................ | B01J 19/0013 |
| 2019/0376190 A1* | 12/2019 | O'Brien | .................... | F02C 3/34 |
| 2021/0340077 A1* | 11/2021 | Schuetzle | ............... | C01B 3/382 |

* cited by examiner

PROCESSES AND APPARATUSES FOR CONVERTING CARBON DIOXIDE INTO OLEFINS

FIELD OF THE INVENTION

This invention relates generally to processes and apparatuses for converting carbon dioxide into olefins.

BACKGROUND OF THE INVENTION

Carbon dioxide is produced in a variety of industrial processes. Often the carbon dioxide is emitted to the atmosphere, however, as carbon dioxide is considered a greenhouse gas, it is desirable, and often required, to reduce the amount of carbon dioxide emitted to the atmosphere.

While carbon dioxide capture technologies are available, there are limited options for using the captured carbon dioxide. Therefore, the captured carbon dioxide requires carbon sequestration. Unfortunately, current transportation and sequestration infrastructure are still lacking the ability to facilitate large scale adoption. Furthermore, the carbon dioxide financial incentives currently available in some countries/regions are not yet at a point where carbon dioxide capture, is economically feasible or desirable.

Accordingly, it would be desirable to have more effective and efficient ways to address carbon dioxide produced.

SUMMARY OF THE INVENTION

One or more processes and apparatuses for converting carbon dioxide into olefins have been invented. The present processes consume the captured carbon dioxide (thereby solving the carbon dioxide use issue) by converting coke into syngas to generate carbon monoxide. The carbon monoxide can subsequently be used for methanol synthesis followed i.e., by light olefins production from the produced methanol.

The present processes and apparatuses include an electrolysis zone which can consume the water generated by the light olefins production to further increase the circularity of this solution. The produced green hydrogen from the electrolysis zone may be used into the methanol synthesis. A power recovery turbine may be utilized to produce electricity, which subsequently can be used to feed the electrolysis section. The electricity could be considered as blue electricity considering the carbon dioxide capture and use.

These present processes and apparatuses provide a green and sustainable outlet for coke, enable the production of olefins from green coal, and contribute to solving the carbon dioxide production problems.

Therefore, the present invention may be generally characterized, in at least one aspect, as providing a process for converting carbon dioxide by: reacting, in a first reaction zone operated under suitable conditions, carbon dioxide with coke to produce carbon monoxide; generating in an electrolysis zone operated under suitable conditions hydrogen from water, and, reacting, in a second reaction zone operated under suitable conditions, the carbon monoxide from the first reaction zone with the hydrogen from the electrolysis zone to produce methanol.

The present invention may also be characterized broadly as providing a process for converting carbon dioxide to hydrocarbons by: passing a coke and a stream comprising carbon dioxide into a first reaction zone, the first reaction zone operated under suitable conditions to produce carbon monoxide, wherein an effluent from the first reaction zone comprises the carbon monoxide; passing a stream comprising water to an electrolysis zone, the electrolysis zone receiving electrical energy and being configured to provide a stream comprising hydrogen; and, passing an effluent stream from the first reaction zone and the stream comprising hydrogen to a second reaction zone, the second reaction zone operated under suitable conditions to produce methanol, wherein an effluent from the second reaction zone comprises the methanol.

In yet a third aspect the present invention may be characterized, broadly, as providing a system for converting carbon dioxide into hydrocarbons having at least: a first reaction zone configured to receive a coke and a stream comprising carbon dioxide and, when operated under suitable conditions, to produce an effluent comprising carbon monoxide; an electrolysis zone configured to receive a stream comprising water and electrical energy and configured to provide a stream comprising hydrogen; and, a second reaction zone configured to receive the effluent from the first reaction zone and the stream comprising hydrogen and, when operated under suitable conditions, to produce methanol, wherein an effluent from the second reaction zone comprises the methanol.

Additional aspects, embodiments, and details of the invention, all of which may be combinable in any manner, are set forth in the following detailed description of the invention.

DETAILED DESCRIPTION OF THE DRAWINGS

Figure 2:
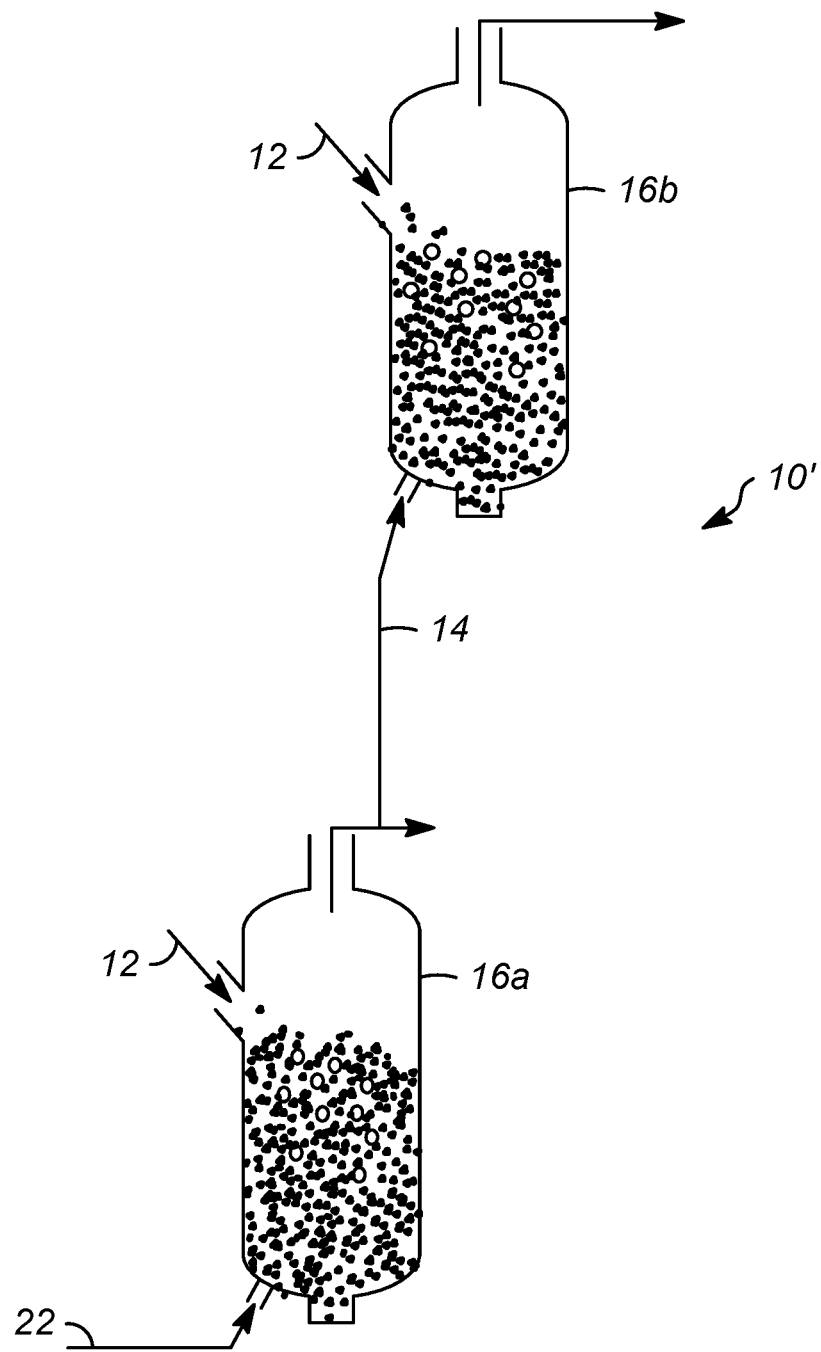

One or more exemplary embodiments of the present invention will be described below in conjunction with the following drawing figures, in which:

FIG. 1 shows an apparatus and process flow diagram according to one of more embodiments of the present invention; and, FIG. 2 shows a first reaction zone that may be utilized in one of more embodiments of the present invention.

DETAILED DESCRIPTION OF THE INVENTION

As mentioned above, processes and apparatuses for converting carbon dioxide into olefins have been invented. In general, coke from various process units may be fed to the fluidized bed reactor in the form of powder or slurry which is contacted with carbon dioxide from other sources. Sand, or other equivalent material, may be used for circulation between a reactor and a regenerator which will carry the heat required to enable the Boudouard reaction (which will be subjected to a 2:1 to 6:1 carbon dioxide to carbon monoxide ratio via a continuous carbon dioxide recycle). The reactor effluent containing carbon monoxide and carbon dioxide is mixed with hydrogen from a water electrolysis zone to generate syngas. The reactor effluent (syngas) is used for methanol synthesis, and the methanol can subsequently be converted to light olefins (propylene/ethylene). Water generated from the methanol to olefin conversion is recycled back to water electrolysis zone. Carbon dioxide from a regenerator in the methanol to olefin conversion can be recycled back to first reactor and oxygen produced from water electrolysis can be passed to the regenerator in the methanol to conversion.

With these general principles in mind, one or more detailed movements of the present invention will now be described with the understanding that the description is not intended to be limiting.

As shown in FIGS. 1 and 2, in a first reaction zone 10, coke 12 is reacted with a stream including carbon dioxide 14 under suitable conditions to produce carbon monoxide. Conditions include a temperature of at least 760° C. (1,400° F.) and a pressure range between 0.1 barg to 10 barg, preferably between 0.1 barg to 5 barg. The sources of the coke may include, for example, delayed coker, coal, sda pitch, steam cracker tar, pyoils, and vacuum fractionation residue.

In the first reaction zone, the carbon monoxide is produced by the Boudouard Reaction:

$$C+CO_2 \rightarrow 2CO \qquad (1).$$

In the embodiment of FIG. 1, the first reaction zone 10 includes a reaction vessel, or reactor, 16 and a regeneration vessel 18. Accordingly, a fuel 20 and an oxygen stream 22, for example air, are passed to a combustion zone 24 to produce heat. An effluent stream 26 from the combustion zone 24 transfers the heat to the regeneration vessel 18, and more particularly to a heat supply media contained therein. The heat supply media may be sand or any solid powder with high thermal conductivity that is mechanically and thermally stable at reaction conditions in fluidized bed regimes Hot heat supply media 28 may be passed to the reaction vessel 16. The reaction vessel 16 receives the carbon dioxide 14 and the coke 12. The hot heat supply media 28 provides the heat for the Boudouard Reaction. An effluent 30 from the first reaction zone 10 contains carbon monoxide. Cool heat supply media 32 may be returned to the regeneration vessel 18. A contaminant removal zone 34 may be included to remove contaminants, for example by desulphurization, denitrification, particulate removal, from the effluent 30 containing carbon monoxide.

A flue gas 36 from the regeneration vessel 18 may be passed to a power recovery turbine 38. In the power recovery turbine 38, the pressure of the flue gas 36 may be reduced while generating electricity 39 (discussed below). The flue gas 36, which contains carbon dioxide, may then be passed to the first reaction zone 10 as a portion of the stream containing the carbon dioxide 14, after water and other gases are removed in a contaminant removal zone 34.

In FIG. 2, the first reaction zone 10' includes a first reaction vessel 16a and a second reaction vessel 16b. In the first reaction vessel 16a, the coke 12 is burned using oxygen 22 to produce carbon dioxide. The stream containing carbon dioxide 14, at a high temperature is sent directly to the second reaction vessel 16b. In the second reaction vessel 16b, coke 12 will react with the carbon dioxide to produce the effluent 30 containing carbon monoxide per Boudouard reaction. The heat requirement for the Boudouard reaction is supplied by burning the coke 12 in the first reaction vessel 16a. The first reactor outlet can be approximately 1,000° C. (1,832° F.) The $2^{nd}$ reactor outlet is expected to be 760° C. (1,400° F.) or higher as the Boudouard reaction tends to stop below 760° C. The remaining portions of FIG. 2 may be the same as FIG. 1.

Thus, returning to FIG. 1, the effluent 30 from the first reaction zone 10, 10' is passed to a second reaction zone 40 which is operated under suitable conditions to produce methanol. In particular, the second reaction zone 40 receives the effluent 30 containing carbon monoxide and a hydrogen 42 and produces methanol via the following reaction:

$$CO+2H_2 \rightarrow CH_3OH \qquad (2).$$

Additionally, the effluent 30 from the first reaction zone 10, 10' will also include carbon dioxide. Accordingly, in the second reaction zone 40, carbon dioxide may also be converted to methanol in the following reaction:

$$CO_2+3H_2 \rightarrow CH_3OH+H_2O \qquad (3).$$

Suitable conditions for the second reaction zone 40 include an operating temperature between 250° to 300° C. (482° to 572° F.) and a pressure between 50 to 100 bar. A copper-zinc oxide-based catalyst is typically used for the above reactions (2) and (3).

The hydrogen 42 consumed in the second reaction zone 40 is produced in an electrolysis zone 44 which is receives electricity 45 and is operated under suitable conditions to generate the hydrogen 42 and oxygen 46 from water 48. The electricity 39 from the power recovery turbine 38 may be sent to the electrolysis zone 44. The oxygen 46 from the electrolysis zone 44 may be used for the stream 22 in first reaction zone 10 and/or as described below.

An effluent 50 from the second reaction zone 40 may be passed to a third reaction zone 52. In the third reaction zone 52, the methanol produced in the second reaction zone 40 may be converted into olefins, such as light olefins including ethylene and propylene, in the following reactions:

$$2CH_3OH \rightarrow CH_3OCH_3+H_2O \qquad (4)$$

$$2CH_3OCH_3 \rightarrow C_2H_4+H_2O \qquad (5)$$

$$3CH_3OCH_3 \rightarrow C_3H_6+2H_2O \qquad (6).$$

Although not shown as such, third reaction zone 52 may include a reactor and a regenerator. The methanol produced from the second reaction zone 40 is passed to the reactor which may be a fluidized bed catalytic reactor which contains a catalyst configured to produce olefins and water via the reactions (4), (5), and (6). A fractionation section may be included downstream to separate an effluent in an olefin stream 54 and a water stream 56. The water stream 56 may be recycled back to the electrolysis zone 44.

Coked catalyst from the reactor may be passed to the regenerator to burn-off the coke. The oxygen 46 from the electrolysis zone 44 may be used for this. Additionally, a gaseous flue gas 58 from the regenerator will contain carbon dioxide. Accordingly, the gaseous flue gas 58 may be recycled back to first reaction zone 10, 10' after separating water and other gases in a contaminant removal zone 34. It is further contemplated that gaseous flue gas 58 from the regenerator can be routed to the power recovery turbine 38 installed in the flue gas 36 from first reaction zone 10, 10'.

Experiments

In a hypothetical economic analysis of a process according to the present invention, in addition to generating revenue from the production of the light olefins, the present invention produces carbon dioxide credit which can be sold. Accordingly, the present invention provides economically desirable processes and apparatus which reduce the emission and sequestration of carbon dioxide.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process for converting carbon dioxide, the process comprising reacting, in a first reaction zone operated under suitable conditions, carbon dioxide with coke to produce carbon monoxide; generating in an electrolysis zone operated under suitable conditions hydrogen from water, and, reacting, in a second reaction zone operated under suitable conditions, the carbon monoxide from the first reaction zone with the hydrogen from the electrolysis zone to produce methanol. An embodiment of the invention is one, any or all of prior embodiments in this paragraph up through the first embodiment in this paragraph, further comprising converting, in a third reaction zone operated under suitable conditions, the methanol from the second reaction zone into light olefins. An embodiment of the invention is one, any or all of prior embodiments in this paragraph up through the first embodiment in this paragraph, wherein the third reaction zone provides an olefin stream and a gaseous stream comprising carbon dioxide. An embodiment of the invention is one, any or all of prior embodiments in this paragraph up through the first embodiment in this paragraph, wherein the gaseous stream comprising carbon dioxide is recycled to the first reaction zone. An embodiment of the invention is one, any or all of prior embodiments in this paragraph up through the first embodiment in this paragraph, further comprising converting, in a third reaction zone operated under suitable conditions, the methanol from the second reaction zone into light olefins, wherein oxygen is passed to the third reaction zone and wherein the oxygen is produced in the electrolysis zone. An embodiment of the invention is one, any or all of prior embodiments in this paragraph up through the first embodiment in this paragraph, wherein the first reaction zone comprises a reaction vessel and a regeneration vessel, wherein a heat supply media is circulated between the reaction vessel and the regeneration vessel. An embodiment of the invention is one, any or all of prior embodiments in this paragraph up through the first embodiment in this paragraph, wherein the first reaction zone comprises a first reaction vessel and a second reaction vessel, the first reaction vessel configured to receive the coke, and the second reaction vessel configured to receive an effluent stream from the first reaction vessel.

A second embodiment of the invention is a process for converting carbon dioxide to hydrocarbons, the process comprising passing a coke and a stream comprising carbon dioxide into a first reaction zone, the first reaction zone operated under suitable conditions to produce carbon monoxide, wherein an effluent from the first reaction zone comprises the carbon monoxide; passing a stream comprising water to an electrolysis zone, the electrolysis zone receiving electrical energy and being configured to provide a stream comprising hydrogen; and, passing an effluent stream from the first reaction zone and the stream comprising hydrogen to a second reaction zone, the second reaction zone operated under suitable conditions to produce methanol, wherein an effluent from the second reaction zone comprises the methanol. An embodiment of the invention is one, any or all of prior embodiments in this paragraph up through the second embodiment in this paragraph, wherein the first reaction zone comprises a reaction vessel and a regeneration vessel, wherein a heat supply media is circulated between the reaction vessel and the regeneration vessel. An embodiment of the invention is one, any or all of prior embodiments in this paragraph up through the second embodiment in this paragraph, further comprising converting, in a third reaction zone operated under suitable conditions, the methanol from the second reaction zone into light olefins. An embodiment of the invention is one, any or all of prior embodiments in this paragraph up through the second embodiment in this paragraph, wherein the electrolysis zone provides a stream comprising oxygen, and wherein the stream comprising oxygen is passed to the third reaction zone. An embodiment of the invention is one, any or all of prior embodiments in this paragraph up through the second embodiment in this paragraph, wherein the third reaction zone provides an olefin stream and a gaseous stream comprising carbon dioxide, and the process further comprising passing the gaseous stream comprising carbon dioxide to the first reaction zone. An embodiment of the invention is one, any or all of prior embodiments in this paragraph up through the second embodiment in this paragraph, further including passing the gaseous stream comprising carbon dioxide provided by the third reaction zone to a power recovery turbine to generate electricity before passing the gaseous stream comprising carbon dioxide to the first reaction zone. An embodiment of the invention is one, any or all of prior embodiments in this paragraph up through the second embodiment in this paragraph, wherein the third reaction zone further provides a water stream, and the process further comprising passing the water stream to the electrolysis zone.

A third embodiment of the invention is a system for converting carbon dioxide into hydrocarbons, the system comprising a first reaction zone configured to receive a coke and a stream comprising carbon dioxide and, when operated under suitable conditions, to produce an effluent comprising carbon monoxide; an electrolysis zone configured to receive a stream comprising water and electrical energy and configured to provide a stream comprising hydrogen; and, a second reaction zone configured to receive the effluent from the first reaction zone and the stream comprising hydrogen and, when operated under suitable conditions, to produce methanol, wherein an effluent from the second reaction zone comprises the methanol. An embodiment of the invention is one, any or all of prior embodiments in this paragraph up through the third embodiment in this paragraph further comprising third reaction zone configured to convert, when operated under suitable conditions, the methanol from the second reaction zone into light olefins. An embodiment of the invention is one, any or all of prior embodiments in this paragraph up through the third embodiment in this paragraph, wherein the electrolysis zone is configured to provide a stream comprising oxygen to the third reaction zone. An embodiment of the invention is one, any or all of prior embodiments in this paragraph up through the third embodiment in this paragraph, wherein the first reaction zone comprises a reaction vessel and a regeneration vessel, wherein a heat supply media is circulated between the reaction vessel and the regeneration vessel. An embodiment of the invention is one, any or all of prior embodiments in this paragraph up through the third embodiment in this paragraph, further comprising a power recovery turbine configured to generate electricity from a flue gas from the regeneration vessel, wherein the electricity generated by the power recovery turbine is provided to the electrolysis zone. An embodiment of the invention is one, any or all of prior embodiments in this paragraph up through the third embodiment in this paragraph, wherein the first reaction zone comprises a first reaction vessel and a second reaction vessel, the first reaction vessel configured to receive the coke, and the second reaction vessel configured to receive an effluent stream from the first reaction vessel. An embodiment of the invention is one, any or all of prior embodiments in this paragraph up through the third embodiment in this paragraph, further comprising a line configured to recycle water from the third reaction zone to the electrolysis zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for converting carbon dioxide, the process comprising:
    reacting, in a first reaction zone having a reactor and a regeneration vessel, operated under suitable conditions, carbon dioxide with coke to produce carbon monoxide;
    circulating a heat supply media between the reactor and the regeneration vessel;
    generating in an electrolysis zone operated under suitable conditions hydrogen from water, and,
    reacting, in a second reaction zone operated under suitable conditions, the carbon monoxide from the first reaction zone with the hydrogen from the electrolysis zone to produce methanol.

2. The process of claim 1, further comprising:
    converting, in a third reaction zone operated under suitable conditions, the methanol from the second reaction zone into light olefins.

3. The process of claim 2, wherein the third reaction zone provides an olefin stream and a gaseous stream comprising carbon dioxide.

4. The process of claim 3, wherein the gaseous stream comprising carbon dioxide is recycled to the first reaction zone.

5. The process of claim 4, further comprising:
    converting, in a third reaction zone operated under suitable conditions, the methanol from the second reaction zone into light olefins,
    wherein oxygen is passed to the third reaction zone and wherein the oxygen is produced in the electrolysis zone.

6. The process of claim 1, wherein the first reaction zone comprises a first reaction vessel and a second reaction vessel, the first reaction vessel configured to receive the coke, and the second reaction vessel configured to receive an effluent stream from the first reaction vessel.

7. A process for converting carbon dioxide to hydrocarbons, the process comprising:
    passing a coke and a stream comprising carbon dioxide into a first reaction zone, the first reaction zone operated under suitable conditions to produce carbon monoxide, wherein an effluent from the first reaction zone comprises the carbon monoxide;
    passing a stream comprising water to an electrolysis zone, the electrolysis zone receiving electrical energy and being configured to provide a stream comprising hydrogen; and,
    passing an effluent stream from the first reaction zone and the stream comprising hydrogen to a second reaction zone, the second reaction zone operated under suitable conditions to produce methanol, wherein an effluent from the second reaction zone comprises the methanol;
    converting, in a third reaction zone operated under suitable conditions, the methanol from the second reaction zone into light olefins, wherein the third reaction zone further provides a water stream;
    passing the water stream to the electrolysis zone.

8. The process of claim 7, wherein the first reaction zone comprises a reaction vessel and a regeneration vessel, wherein a heat supply media is circulated between the reaction vessel and the regeneration vessel.

9. The process of claim 7, wherein the electrolysis zone provides a stream comprising oxygen, and wherein the stream comprising oxygen is passed to the third reaction zone.

10. The process of claim 7, wherein the third reaction zone provides an olefin stream and a gaseous stream comprising carbon dioxide, and the process further comprising:
passing the gaseous stream comprising carbon dioxide to the first reaction zone.

11. The process of claim 10, further comprising:
passing the gaseous stream comprising carbon dioxide provided by the third reaction zone to a power recovery turbine to generate electricity before passing the gaseous stream comprising carbon dioxide to the first reaction zone.

12. A system for converting carbon dioxide into hydrocarbons, the system comprising:
a first reaction zone, comprising a reaction vessel and a regeneration vessel, configured to receive a coke and a stream comprising carbon dioxide and, when operated under suitable conditions, to produce an effluent comprising carbon monoxide;
an electrolysis zone configured to receive a stream comprising water and electrical energy and configured to provide a stream comprising hydrogen; and,
a second reaction zone configured to receive the effluent from the first reaction zone and the stream comprising hydrogen and, when operated under suitable conditions, to produce methanol, wherein an effluent from the second reaction zone comprises the methanol,
wherein a heat supply media is circulated between the reaction vessel and the regeneration vessel.

13. The system of claim 12 further comprising:
third reaction zone configured to convert, when operated under suitable conditions, the methanol from the second reaction zone into light olefins.

14. The system of claim 13, wherein the electrolysis zone is configured to provide a stream comprising oxygen to the third reaction zone.

15. The system of claim 12, further comprising:
a power recovery turbine configured to generate electricity from a flue gas from the regeneration vessel, wherein the electricity generated by the power recovery turbine is provided to the electrolysis zone.

16. The system of claim 12, wherein the first reaction zone comprises a first reaction vessel and a second reaction vessel, the first reaction vessel configured to receive the coke, and the second reaction vessel configured to receive an effluent stream from the first reaction vessel.

\* \* \* \* \*